(12) United States Patent
Hansen (10) Patent No.: US 8,608,684 B2
(45) Date of Patent: Dec. 17, 2013

(54) IMPULSE CHAMBER FOR JET DELIVERY DEVICE

(75) Inventor: Torben Strøm Hansen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 1374 days.

(21) Appl. No.: 11/439,898

(22) Filed: May 24, 2006

(65) Prior Publication Data

US 2007/0049864 A1  Mar. 1, 2007

Related U.S. Application Data

(63) Continuation of application No. PCT/DK2004/000817, filed on Nov. 25, 2004.

(60) Provisional application No. 60/526,829, filed on Dec. 4, 2003.

(30) Foreign Application Priority Data

Nov. 27, 2003  (DK) .................................. 2003 01751

(51) Int. Cl.
*A61M 5/30* (2006.01)
*A61M 37/00* (2006.01)

(52) U.S. Cl.
USPC ............................................ 604/71; 604/131

(58) Field of Classification Search
USPC ................ 604/68–72, 140–148, 131
See application file for complete search history.

(56) References Cited

U.S. PATENT DOCUMENTS

| | | | |
|---|---|---|---|
| 2,653,603 A * | 9/1953 | Hein, Jr. ......................... | 604/71 |
| 2,704,542 A | 3/1955 | Scherer | |
| 2,737,946 A | 3/1956 | Hein | |
| 3,507,276 A | 4/1970 | Burgess | |
| 4,059,107 A | 11/1977 | Iriguchi et al. | |
| 4,447,225 A * | 5/1984 | Taff et al. ......................... | 604/71 |
| 4,747,834 A | 5/1988 | Prindle | |
| 5,026,343 A | 6/1991 | Holzer | |

(Continued)

FOREIGN PATENT DOCUMENTS

| | | |
|---|---|---|
| CA | 2214468 | 3/1999 |
| DE | 10137962 | 2/2003 |
| EP | 1161961 | 12/2001 |
| EP | 879609 | 7/2002 |
| EP | 1277487 | 1/2003 |
| EP | 1514565 | 3/2005 |

(Continued)

OTHER PUBLICATIONS

Adler, Norman, "*Use of Self-Sealing Elastomer Septums for Quantitative Operations with Volatile Solvents*," (vol. 36, No. 12, Anal. Chem., pp. 2291-2295, Nov. 1964).

*Primary Examiner* — Theodore Stigell
*Assistant Examiner* — Nathan R Price
(74) *Attorney, Agent, or Firm* — Wesley A. Nicolas; Marc A. Began; Reza Green (57) ABSTRACT

The invention provides a jet expelling assembly comprising a reservoir and an impulse chamber assembly. The impulse chamber assembly comprises a chamber portion defining a cavity having a general axis, a piston received in the cavity along the general axis and comprising a fluid inlet, thereby defining a variable-volume impulse chamber with an outlet nozzle. The inlet comprises a conduit adapted to slidably engage a reservoir outlet during relative movement therebetween. The chamber portion is arranged stationary relative to the reservoir, whereby expelling an amount of drug from the reservoir to the impulse chamber via the inlet causes the piston to move towards the reservoir, the impulse chamber thereby receiving the expelled amount of drug.

18 Claims, 3 Drawing Sheets

(56) References Cited

U.S. PATENT DOCUMENTS

| | | | |
|---|---|---|---|
| 5,190,523 | A | 3/1993 | Lindmayer |
| 5,480,381 | A | 1/1996 | Weston |
| 5,840,062 | A | 11/1998 | Gumaste et al. |
| 5,879,336 | A | 3/1999 | Brinon |
| 6,056,728 | A | 5/2000 | von Schuckmann |
| 6,213,980 | B1 | 4/2001 | Colburn et al. |
| 6,235,004 | B1 | 5/2001 | Steenfeldt-Jensen et al. |
| 6,689,092 | B2 * | 2/2004 | Zierenberg et al. ............. 604/68 |
| 2002/0007142 | A1 | 1/2002 | Hjertman et al. |
| 2002/0022804 | A1 | 2/2002 | Connolly et al. |
| 2002/0055707 | A1 | 5/2002 | Slate et al. |
| 2002/0065483 | A1 | 5/2002 | Leon et al. |
| 2003/0083611 | A1 | 5/2003 | Angel et al. |
| 2004/0129803 | A1 | 7/2004 | Dolder et al. |
| 2007/0049873 | A1 | 3/2007 | Hansen et al. |

FOREIGN PATENT DOCUMENTS

| | | |
|---|---|---|
| FR | 2339407 | 8/1977 |
| GB | 879427 | 10/1961 |
| GB | 2187962 | 3/1986 |
| JP | 2001-346878 | 6/2000 |
| WO | WO 01/30419 | 5/2001 |
| WO | WO 01/37907 | 5/2001 |
| WO | WO 01/47586 | 7/2001 |
| WO | WO 01/89614 | 11/2001 |
| WO | WO 02/49697 | 6/2002 |
| WO | WO 02/053214 | 7/2002 |
| WO | WO 02/076542 | 10/2002 |
| WO | WO 03/000320 | 1/2003 |
| WO | WO 03000318 A1 * | 1/2003 |
| WO | WO 03/105934 | 12/2003 |
| WO | WO 2004/039438 | 5/2004 |
| WO | WO 2005/051465 | 6/2005 |
| WO | WO 2007/122193 | 11/2007 |

* cited by examiner

IMPULSE CHAMBER FOR JET DELIVERY DEVICE

CROSS-REFERENCE TO RELATED APPLICATIONS

This application is a continuation of International Application Number: PCT/DK2004/000817, filed Nov. 25, 2004, which claims priority to Danish Patent Application Number PA 2003 01751, filed Nov. 27, 2003, and U.S. Provisional Application No. 60/526,829, filed Dec. 4, 2003, the contents of each of which is incorporated herein in its entirety.

The invention relates to an impulse chamber which can be used for expelling an amount of a fluid compound from a reservoir at a high pressure. The impulse chamber may be used e.g. in a skin-penetrating jet injection device or it may be used as a nebulizing means in an inhalation device e.g. for pulmonary administration of a drug.

BACKGROUND OF THE INVENTION

Subcutaneous and intramuscular delivery of liquid drugs by injection is common in the medical arts. As some medications, such as insulin, must be given frequently by injection to an individual, it is desirable that the injections can be performed easily.

Many patients dislike needle injections due to pain or fear for needles. Further, blood-borne pathogens, such as HIV and hepatitis, can be transmitted to health care workers by accidental needle-sticks. Also, the disposal of used needles is a growing concern. This disposal presents a problem to individuals other than healthcare workers. Children, for example, may find used needles in the trash, putting them at risk of contracting infection. Discarded needles likewise pose a risk to waste disposal workers.

In efforts to minimize the fears and risks associated with needle injections, several types of needle-free jet injectors have been developed. These devices penetrate the skin using a high velocity fluid jet, and deliver medication into the tissue of a patient. In order to accomplish this, a force is exerted on the liquid medication. Jet injectors, in general, contain a fluid drug which has been transferred into a chamber having a small orifice at one end. A driver, e.g. a ram, is accelerated using either a coil spring or a compressed gas energy source. The ram impacts a plunger, which in turn creates a high pressure impulse within the chamber. This pressure impulse ejects the fluid medicament through the orifice at high velocity, piercing the skin. The energy source continues to apply a force to the plunger, which quickly propels the drug through the opening in the skin, emptying the syringe in a fraction of a second. The driver may be adapted to provide a two-stage injection, i.e. a first penetrating burst of drug at a high pressure followed by a subsequent delivery of the remaining amount of drug at a lower pressure.

Injectable drugs may be supplied in glass vials sealed with an inert rubber stopper. To administer the fluid drug, the user must transfer the fluid drug from the vial to a fluid drug delivery device, such as a syringe and needle, or a needleless jet injector syringe. Transferring the fluid drug adds cost to administering injections in a hospital or clinic because of the labor expense. Immunizing large populations requires administering many injections per hour, hence transferring the fluid drug presents a significant time constraint. For the patient who must self-administer fluid drugs, such as a diabetic patient requiring several insulin injections a day, transferring the fluid drug can be an inconvenience. Also, with each transfer, there is an opportunity for error in the amount of fluid drug being transferred and administered.

In an effort to eliminate transferring a fluid drug from a vial, pre-filled glass cartridges have been developed. These pre-filled cartridges are similar in design to a syringe. One end is closed and includes either a needle or an inert rubber septum. If a needle is not integral, then a needle subassembly that penetrates the rubber septum is attached prior to use. A movable rubber piston closes the end opposite the needle. To administer the fluid drug, the pre-filled cartridge is placed in a device consisting of a holder and a driver that meets the movable rubber plunger. The user depresses the plunger to dispense the medication.

An example of the use of pre-filled cartridges is in the treatment of diabetes with multiple daily injections of insulin by use of an injection device, e.g. pen-shaped, in which a pre-filled cartridge containing an amount of insulin sufficient for several days can be mounted, the injection device comprising means for setting a desired dose and subsequently expelling the dose. A disadvantage of pre-filled cartridges, however, is that they still require using a needle to penetrate the skin and deliver the medication to the target tissue.

Neither glass vials containing multiple doses of a drug nor pre-filled cartridges can be used with traditional jet injectors. For example, if the force generated by the jet injector drive means was applied directly to the piston the cartridge would in most cases burst. This is because a significant amount of impulse energy is transmitted from the energy source. Although not directly impacted, the glass walls of the cartridge do not have sufficient strength to withstand the large amplitude pressure waves that result when the ram impacts the piston.

Addressing this problem, US patent application 2002/0055707 discloses a jet injection device comprising a reservoir in the form of prefilled drug cartridge, an impulse chamber to which an amount of drug to be expelled by jet action is transferred through a fluid connection between the reservoir and the impulse chamber. The impulse chamber has an injection nozzle at a distal end, and a drive piston adapted to engage a ram member at the proximal end. JP-2001-346878A discloses a similar arrangement in which the drug cartridge is in fluid communication with the impulse chamber through an inlet opening in the impulse piston, fluid communication between the opening and the cartridge being provided by a flexible hose member. U.S. Pat. No. 3,507,276 discloses a jet injector comprising an impulse chamber with a piston, a reservoir being attached to the piston with the piston and reservoir moving as a unit, and WO 2003/105934 discloses an impulse chamber unit with a fixed inlet and a moveable internal piston.

In view of the above, it is an object of the present invention to provide an impulse chamber configuration which allows a cartridge (e.g. conventional) to be used in combination with a jet injection (or nebulizing) device. In the alternative, it is a further object to provide an impulse chamber unit which can be used in combination with a jet injection device adapted to receive a conventional cartridge containing a liquid drug, the impulse chamber unit being simple and compact in design, thus allowing for cost-efficient manufacture, e.g. as a single-use disposable unit.

In the alternative, it is an object to provide an impulse chamber with a nozzle which can be placed against the skin of a subject, the configuration of the impulse chamber allowing for visual inspection of the jet injection site.

In the alternative, it is an object of the invention to provide an impulse chamber and reservoir configuration which allows a small and handy jet injection device to be provided.

In the alternative, it is an object to provide a jet injection device that can be modeled similar in function and form with a conventional pen type injector, to make the patient comfortable with the jet injection device, and so that the jet injection device can easily be utilized by a non-professional user, e.g. a insulin requiring diabetic.

DISCLOSURE OF THE INVENTION

In the disclosure of the present invention, embodiments will be described which will address one or more of the above objects or which will address objects apparent from the below disclosure as well as from the description of exemplary embodiments.

Correspondingly, in a first aspect a jet expelling assembly is provided, comprising a housing, a reservoir adapted to contain a fluid drug and comprising an outlet, and an impulse chamber assembly. The impulse chamber assembly comprises a chamber portion defining a cavity, a piston slidably received in the cavity along a general axis and comprising a fluid inlet, the cavity and the piston in combination defining a variable-volume impulse chamber, the inlet comprising a generally straight conduit protruding from the piston and arranged generally parallelly with the general axis, the conduit being adapted to slidably engage the reservoir outlet during relative movement therebetween, and a fluid outlet nozzle in fluid communication with the impulse chamber. The chamber portion is arranged stationary relative to the reservoir such that expelling of an amount of drug from the reservoir to the impulse chamber via the inlet causes the piston to move towards the reservoir, the impulse chamber thereby receiving the expelled amount of drug.

As appears, by this arrangement only the piston will have to be moved relative to the reservoir and the nozzle during filling respectively emptying of the impulse chamber, this allowing for a compact and simple design. By this design a very compact chamber unit can be provided in which the fluid communication can be integrated with the volume-varying structures.

The term "nozzle" does not imply that a singular nozzle opening is defined, i.e. the impulse chamber may comprise a number or a system of nozzle openings. In accordance with the intended use, the nozzle(s) may be configured to e.g. provide a well-defined jet of liquid for skin-penetration or an aerosol for inhalation.

In exemplary embodiments a conduit is arranged generally co-axially with the general axis, just as the fluid outlet nozzle may be arranged generally in parallel with the general axis, e.g. co-axially.

The reservoir outlet may comprise a self-sealing septum cooperating with a conduit comprising a pointed proximal end adapted to penetrate the self-sealing septum. The conduit may be formed integrally with the piston, e.g. as a unitary polymer unit, or it may be provided as a separate member mounted to the piston, e.g. a hollow steel needle.

To prevent excessive back-flow of fluid from the impulse chamber during actuation of the piston to empty the impulse chamber, the fluid inlet may comprise a uni-directional inlet valve, a narrow flow restriction or a tortuous path portion. However, the fluid inlet may be "open" to allow an amount of drug to be forced backwardly into the reservoir during expelling of drug from the impulse chamber, the flow resistance of the outlet nozzle, the flow resistance of the fluid inlet and the impulse generating assembly being configured to allow a backflow of less than 15%, preferably less than 10%, more preferably less than 5% and most preferably less than 1%.

When used as a jet injection device, the fluid outlet nozzle may be provided with a pointed hollow needle adapted to penetrate a superficial layer of the skin of a user, thereby aiding the jet of drug to create an opening in the skin from the surface to the subcutaneous space. Such a needle may be relatively short, e.g. 1 mm or less.

The above-described assembly may used in combination with an impulse and/or drive assembly, the two assemblies being adapted to be releasably connected to each other. Alternatively a unitary device may be provided.

Thus, in an exemplary embodiment a jet expelling assembly further comprises means for expelling an amount of drug from the reservoir to the impulse chamber via the fluid inlet thereby expanding the impulse chamber, and impulse generating means adapted to actuate the piston to thereby reduce the volume of the impulse chamber, thereby expelling an amount of drug through the outlet nozzle. When adapted for jet injection, the fluid outlet nozzle is adapted to be arranged against the skin of a subject, the impulse generating means being adapted to create a force for injecting the liquid drug from said impulse chamber, through the outlet nozzle and into the subject through the skin.

When initially an opening has been created in the skin, a lower force can be used to inject a remaining drug dose through the opening for which reason the jet expelling device may further comprise drive means for reducing the volume of the impulse chamber with a reduced force relative to the impulse generating means when the latter has been actuated.

In an exemplary embodiment a jet expelling assembly further comprises means for selectable setting a dose of drug to be expelled and transfer that amount of drug to the impulse chamber, means for actuating the impulse generating means and the drive means, and actuatable release means. When the release means is actuated it first causes release of the impulse generating means thereby expelling a portion of the set dose from the impulse chamber at a high pressure through the outlet nozzle, followed by release of the drive means for subsequent expelling of the remaining portion of the set dose from the impulse chamber through the outlet nozzle.

The impulse and/or drive means may be driven my any suitable means such as one or more springs or by compressed gas. When the impulse generating means comprises a coil spring it may advantageously be arranged substantially axially relative to the general axis, e.g. surrounding the impulse chamber and/or a portion of the reservoir.

The jet expelling assembly of the present invention may be in the form of disposable device adapted for single use, or it may be in the form of a nebulizing device adapted to be used a limited number of times. For such a use the impulse chamber may be formed integrally with the reservoir. However, if the assembly is intended as a jet injection device for repeated use, the impulse chamber assembly may be releasably attached relative to the housing, this allowing the nozzle portion to be renewed before each injection. When the assembly is intended for durable use, the reservoir can be releasably attached relative to the housing. In exemplary embodiments, the reservoir has a general columnar configuration with a longitudinal axis arranged co-axially with the axis defined by the movement of the piston. Independent of the type of jet expelling assembly, the impulse chamber assembly may be releasably attached relative to the housing allowing a new impulse chamber assembly to be used for each jet injection.

In a further aspect of the invention, an impulse chamber unit is provided comprising a variable-volume impulse chamber adapted for containing a volume of a flowable drug. The unit comprises a fluid outlet nozzle in fluid communication with the impulse chamber, and a fluid inlet in fluid communication with the impulse chamber, wherein the fluid inlet comprises a generally straight conduit protruding from the impulse chamber unit.

In an exemplary embodiment the volume-variation of the impulse chamber results in the fluid outlet nozzle and the fluid inlet being displaced relative to each other.

In a further exemplary embodiment the impulse chamber has a proximal end and a distal end, wherein the fluid outlet nozzle extends in the distal direction, the conduit member protrudes in the proximal direction, with the fluid outlet nozzle and the fluid inlet being arranged generally co-axially, such that volume-variation of the impulse chamber results in the fluid outlet nozzle and the conduit member being displaced relative to each other corresponding to their axial directions.

The impulse chamber may comprise a first chamber portion comprising the fluid outlet nozzle, and a second chamber portion comprising the fluid inlet, the first and second chamber portion in combination defining the impulse chamber. Advantageously the first chamber portion is in the form of a housing portion defining a cylindrical cavity, and the second chamber portion is in the form of a piston slidably received in the cavity.

Depending on the intended use of the impulse chamber, preferably either the inlet or outlet is moveable relative to the device in which it is adapted to be arranged. For example, when the outlet nozzle is adapted to be arranged against the skin of the user, it should be stationary relative thereto. Thus, in a preferred embodiment the fluid inlet comprises a pointed proximal end adapted to penetrate a self-sealing septum member of a fluid supply (e.g. a traditional cartridge). Depending on the actual design of the device in combination with which the impulse chamber is to be used, the inlet may be provided with unidirectional inlet valve or a tortuous path portion protecting the reservoir from the pressure wave generated during jet expelling.

In a further aspect of the invention a method for expelling an amount of drug is provided, the method comprising the steps of providing a jet expelling assembly comprising a drug reservoir with an inlet, a variable-volume impulse chamber with an axially displaceable piston, the piston comprising an inlet in sliding engagement with the reservoir outlet, and a nozzle in fluid communication with the impulse chamber, the method comprising the further step of expelling an amount of drug from the reservoir to the impulse chamber thereby moving the piston relative to the reservoir and the nozzle. The piston may then be moved relative to the reservoir and the nozzle to expel an amount of drug from the impulse chamber through the nozzle.

In a yet further aspect a jet injection assembly is provided comprising an impulse chamber unit as described above, in combination with a jet injection device and a reservoir mounted relative thereto, wherein the reservoir is adapted to contain (or contains) a liquid drug and comprises an outlet allowing the fluid inlet to be arranged in fluid communication with an interior of the reservoir, the jet injection device comprising means for expelling an amount of drug from the reservoir to the impulse chamber via the fluid inlet thereby expanding the impulse chamber. To expel an amount of drug through the outlet nozzle the jet injection device comprises impulse generating means for reducing the volume of the impulse chamber.

In an exemplary embodiment adapted for use as a jet injection device for drug skin penetration, the impulse chamber unit comprises a housing portion defining a cavity with a general axis and with a jet outlet nozzle, and a piston slidably received in the cavity, the piston comprising fluid inlet, such that the cavity and the piston in combination define the impulse chamber. The housing portion is arranged stationary relative to the reservoir and the piston is arranged slidably relative to the reservoir, and the fluid inlet is adapted to allow movement of the piston relative to the reservoir, such that expelling an amount of drug from the reservoir to the impulse chamber via the fluid inlet causes the piston to move towards the reservoir, the impulse generating means being arranged to move the piston away from the reservoir thereby expelling an amount of drug from the impulse chamber. In such a device the outlet nozzle is adapted to be arranged against the skin of a subject and the impulse generating means is adapted to create a force for injecting said fluid drug from the impulse chamber, through the outlet nozzle and into the patient through the skin.

In an exemplary embodiment the fluid inlet comprises a generally straight conduit member projecting from the piston and adapted to slidably engage the reservoir outlet during relative movement therebetween, the conduit member being arranged generally co-axially with the general axis, the piston member being arranged to move corresponding to the general axial direction.

Preferably the reservoir outlet is in the form of a self-sealing needle-penetratable septum and the straight conduit member is in the form of a pointed hollow needle member capable of slidably engaging the septum.

To provide a compact design resembling the appearance of traditional pen-formed injection device, the reservoir may have a general columnar configuration with a longitudinal axis arranged co-axially or axially with the general axis. Further, the impulse generating means may comprise a coil spring arranged substantially axially relative to the general axis, the coil spring surrounding at least a portion of the reservoir or the impulse chamber.

As used herein, the term "drug" is meant to encompass any drug-containing flowable medicine or medicament capable of being passed through a nozzle under high pressure in a controlled manner, such as a liquid, solution, gel or fine suspension. Representative drugs include but is not limited to pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" injection is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein.

In the figures like structures are primarily identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
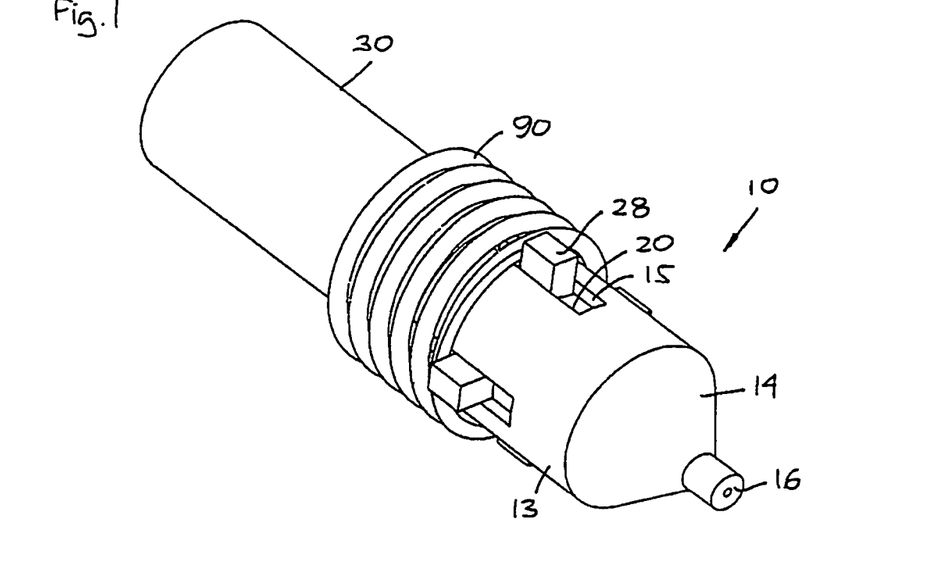
FIG. 1 is a schematic, perspective view of a part of a jet injection device comprising an impulse chamber unit.

FIG. 1 shows a perspective view of an impulse chamber unit 10 in combination with a drug cartridge 30 and a coil spring 90, the latter representing a portion of impulse generating means (not shown in full).

Figure 2:
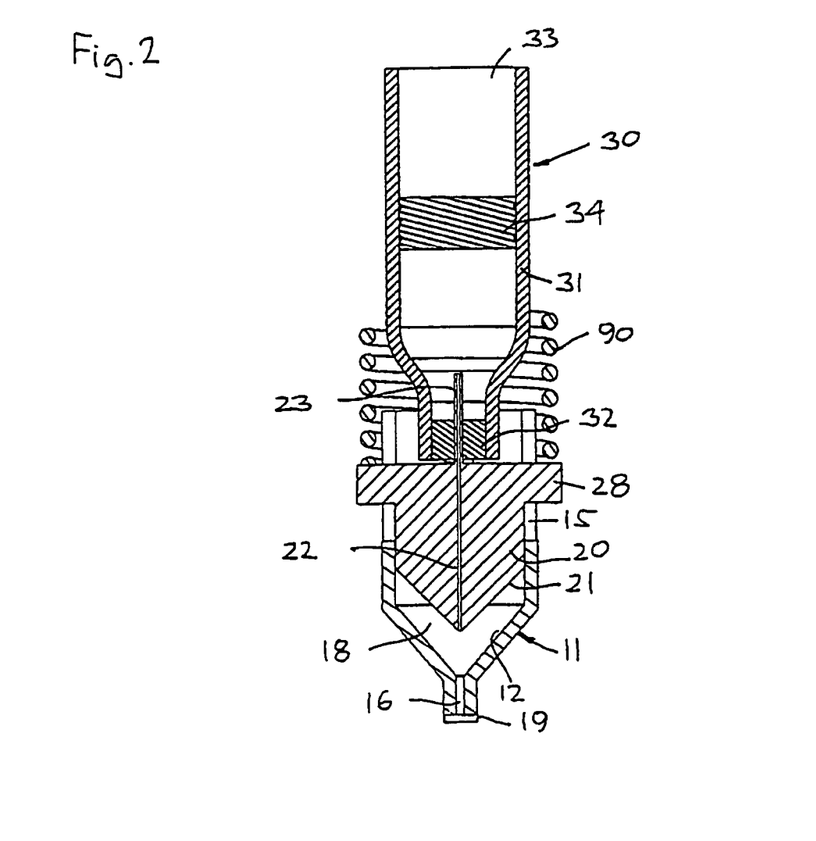
FIG. 2 is a sectional view taken along a central plane through the jet injection device shown in FIG. 1, FIG. 3. is a sectional view taken along a central plane through a further jet injection device.

Turning to FIG. 2, the impulse chamber unit 10 comprises a housing member 11 defining an interior cavity 12, the housing having a generally cylindrical main portion 13 with a conical distal end portion 14 and a proximal opening. A number of longitudinal slots 15 are formed in the proximal portion of the housing, the slots extending to the proximal end. In the distal end an outlet nozzle 16 is formed in fluid communication with the interior of the cavity. Prior to use, the nozzle is closed by a seal member 19 shown schematically.

A mating impulse piston 20 is slidably received in the housing, the piston comprising a conical distal surface 21 corresponding to the distal portion of the housing, whereby a variable volume impulse chamber 18 is defined by the inner surface of the distal portion of the housing member and the distal surface of the piston, the piston being moveable along an axis. Due to the corresponding configurations of the distal portions of the piston and the housing member, the volume of the impulse chamber is substantially zero when the piston is in its foremost position. From the proximal end of the piston projects a hollow needle-formed extension 23 with a proximal opening which is in flow communication with a conduit 22 formed axially through the piston and having a distal opening arranged on the distal surface of the piston, the conduit in the piston and the needle-formed extension in combination forming a fluid inlet for the impulse chamber. As appears the extension and the piston form a unit which can be moved relative to a reservoir outlet. The needle-formed extension may be a separate member, e.g. a metal conduit, or it may be formed integrally with the piston from a suitable polymer as shown. Independent of the actual configuration and construction of the extension, it may be denoted a "back needle". Further, the needle-formed extension extends co-axially with the axis of piston movement. In the shown embodiment the needle-formed extension is arranged corresponding to a central axis common for the piston and the housing. The piston further comprises a number of radial projections 28 adapted to be slidably received in the slots formed in the housing, the projections serving as an interface with the means for driving the piston forwardly (see below).

A cartridge 30 containing a liquid drug to be expelled is connected to the piston, the shown cartridge having a general configuration corresponding to a typical standard cartridge used for e.g. insulin. More specifically, the cartridge comprises a columnar housing portion 31 with a distal opening closed by a self-sealing needle-penetratable septum 32 (e.g. made by a rubber compound), and a proximal opening 33. A piston 34 is arranged within the housing, the interior wall of the housing, the septum and the piston defining a variable-volume reservoir for containing a liquid drug. In the shown embodiment the cartridge has been mounted relative to the housing member 11 (by means not shown) with the needle-formed extension of the piston slidably arranged through the septum. Preferably the extension has a pointed proximal end (not shown) adapted to penetrate the septum. As appears, the outlet of the reservoir may be closed until fluid communication is established between the reservoir and the impulse chamber.

FIGS. 1 and 2 further show a coil spring 90 arranged co-axially relative to the cartridge and the impulse chamber, the spring having a distal end in engagement with the radial projections 28 of the impulse piston 20.

In the following a situation of use will be described. First the cartridge is mounted in the jet injectoin device by means not shown (in fact, in the figures only the coil spring represents the jet injection device) a plunger (also not shown) being arranged in through the distal opening of the cartridge engaging the piston 34. The cartridge may e.g. contain insulin. Thereafter a new impulse chamber unit is mounted with the housing member thereof fixedly arranged relative to the cartridge and the jet injection device, the needle-formed extension thereby penetrating the septum. When supplied to the user, the impulse piston is in its foremost position and the outlet nozzle is closed by a user-removable seal member. Thereafter the plunger is moved forwardly to expel a given amount of drug from the cartridge to the impulse chamber (e.g. using a dose setting mechanism, not shown), this resulting in the impulse piston being forced rearwards as the chamber is filled, the sliding engagement between the needle extension and the septum allowing this movement. During this initial filling procedure, in which the impulse may be fully or only partially filled, the coil spring is preferably de-coupled from the impulse chamber. The impulse generating means for reducing the volume of the impulse chamber (here the coil spring) to thereby expel the drug from the impulse chamber may be actuated (e.g. compressed) either before, after or simultaneously with the filling procedure.

The injection device is now ready for injection, the seal member can be removed (may e.g. be attached either by adhesive or by a threaded connection) and the nozzle can be placed against the skin of a subject at a suitable location. To initiate an injection, the impulse generator is released thereby driving forward the impulse piston whereby the fluid drug in the impulse chamber is forced from the impulse chamber through the nozzle and punctures the skin of the subject. As appears from the figures the impulse chamber is in permanent fluid communication with the reservoir which means that the drug is forced not only out through the nozzle but is also forced rearwards through the inlet conduit back in the reservoir. Indeed, this is not desirable for which reason the flow resistance of the inlet and outlet openings should be chosen such that only an acceptable small volume of drug (if any) is transferred back to the reservoir. Dependent e.g. upon the pressure generated in the impulse chamber by the impulse generator, the duration of the injection, the viscosity of the liquid drug and the configuration of the nozzle and the fluid inlet, the flow resistance in the nozzle and the fluid inlet should be chosen in accordance with the desired properties for the jet injection assembly. For example, the flow resistance in the nozzle and the fluid inlet may be chosen to allow a backflow of e.g. less than 1%, less than 5%, less than 10% or less than 15% for a given configuration of a jet injection assembly.

As appears from FIG. 2 is the combined fluid inlet 22, 23 in the shown embodiment straight, however, to protect the cartridge from the pressure wave generated during jet injection, the fluid inlet may be non-straight, e.g. kinked or tortuous which configuration would also raise the flow resistance during jet injection. To even more effectively protect the cartridge from pressure waves and to ideally prevent any backflow, the fluid inlet may be provided with check valve, e.g. a lip or ball valve.

The jet injection itself may be one-stage or two-stage. In a one-stage injection the entire volume to be injected is expelled with substantially the same pressure, whereas in two-stage injection a first smaller amount is injected under a very high pressure to puncture the skin, followed by (typically) subcutaneous injection of the "main" volume of drug. Two-stage injection may be accomplished in a number of ways. For example, having regard to the shown embodiment, the entire volume to be injected may be transferred to the impulse chamber which is then subjected to a first, short impulse generating a very high puncturing pressure followed by a second, longer "expelling impulse". Many different arrangement may be used to achieve this, e.g. using two springs or a spring in combination with a gas/compressed air drive arrangement, however, the specific nature of the driving means is not within the scope of the present invention. In an alternative configuration only the amount of drug necessary for the first stage is transferred to the impulse chamber, the main volume being expelled from the cartridge through the fluid inlet of the impulse piston.

Advantageously the drive means for the two stages are both actuated and released in accordance with a coupled mechanism this providing a device which is simple to use. For example, the jet expelling device may comprise drive means for reducing the volume of the impulse chamber with a reduced force relative to the impulse generating means, as well as means for selectable setting a dose of drug to be expelled, means for actuating the impulse generating means and the drive means, and actuatable release means, whereby actuation of the release means first causes release of the impulse generating means thereby expelling a portion of the set dose at a high pressure through the outlet nozzle, followed by release of the drive means for subsequent expelling of the remaining portion of the set dose through the outlet nozzle.

Figure 3:
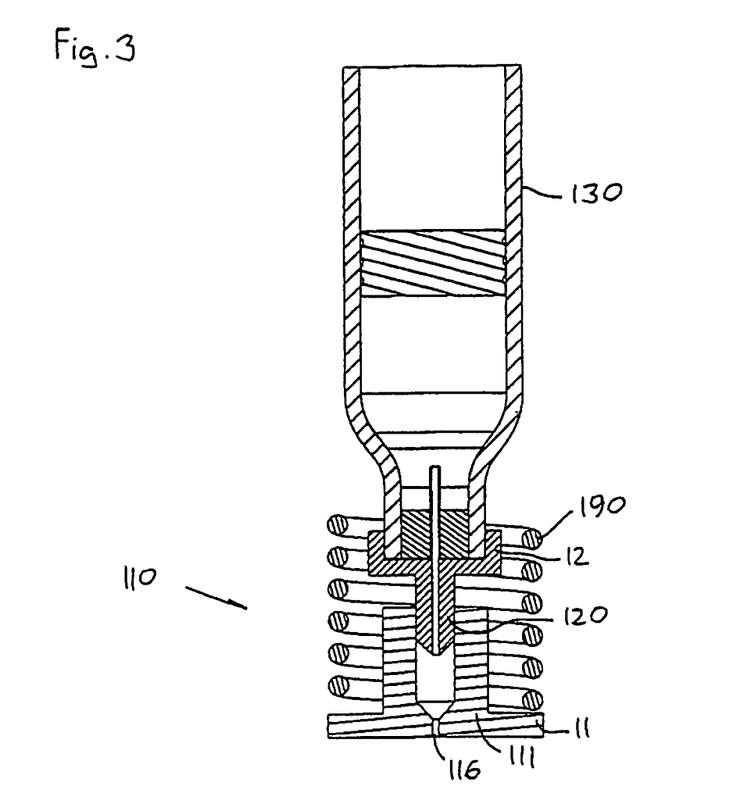

FIG. 3 shows a sectional view of a second embodiment of an impulse chamber unit 110, comprising a housing member 111 and an impulse piston 120, in combination with a drug cartridge 130 and a coil spring 190, the latter representing a portion of impulse generating means. In the first embodiment the nozzle was adapted to be arranged against the skin of a subject for which reason the housing member with the nozzle was arranged stationary relative to the drug cartridge and the jet injection device, the impulse chamber volume variation being provided by the slidably arranged impulse piston. In contrast, in the second embodiment the impulse chamber is mounted stationary onto the cartridge with the housing member being slidable relative thereto such a configuration being suitable for an inhalation device in which the purpose of the impulse chamber and the nozzle 116 would be to create an aerosol of drug droplets to be inhaled. Correspondingly, the impulse piston comprises an axially extending circumferential flange portion 127 allowing it to be mounted on the cartridge, and the housing member comprises a radially extending flange portion 117 allowing the coil spring 190 to engage the housing member. Otherwise the configuration of the impulse chamber unit 110 is similar to the first embodiment.

In a situation of use, when an amount of drug is transferred from the cartridge, the housing member is moved distally. In the shown arrangement the impulse generating means is a "pull" coil spring 190 which when released moves the housing member and thus the needle proximally thereby creating an aerosol of drug from the nozzle.

Although the "stationary nozzle" configuration of the first embodiment is especially suitable for jet injection through the skin, it will be correspondingly suitable for use in an inhalation device.

The housing member 11, 111 for the impulse chamber unit can be formed from a metal or a metal alloy, or it can be formed from a plastic or polymer material (e.g. a polycarbonate material), with a rigidity and strength suitable for withstanding the high pressure created during the drug expelling.

The impulse piston may be formed from a rubber or polymer material with the needle extension formed from a metal or a metal alloy, or it can be formed from a polymer material, advantageously unitary with the piston.

The impulse chamber of the present invention may be used with a standard, pre-filled glass cartridge as described, with a corresponding cartridge formed from a polymer, or with any other type of reservoir, e.g. a flexible reservoir in the form of a prefilled, flexible pouch.

Figure 4:
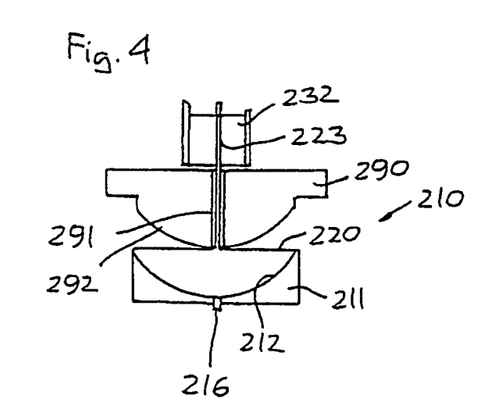
FIGS. 4 and 5 show two further embodiments of impulse chamber units.

In FIG. 4 a further embodiment of an impulse chamber unit 210 is shown. The unit comprises a housing member 211 forming a concave cavity 212, the cavity being covered by a flexible diaphragm 220 thereby defining an impulse chamber 218 having a nozzle 216 formed in the housing and a fluid inlet in the form of a protruding rear needle 223 extending from the diaphragm and into the septum 232 of a cartridge. The nozzle is in the form of a pointed hollow needle adapted to penetrate a superficial layer of the skin of a user. A drive piston 290 having a central bore 291 is arranged slidably relative to the housing member, the back needle being arranged through the bore, this allowing the diaphragm to move axially relative to both the housing member, the drive piston and the septum (as in the first embodiment). The drive piston has a distal surface 292 corresponding to the concave impulse chamber. When the impulse chamber is filled the diaphragm is displaced proximally, where after the drive chamber is released to drive the diaphragm into engagement with the housing portion. In this way the diaphragm functions as a piston for thereby expelling drug from the impulse chamber. The sliding drive piston may be supplied as part of the impulse chamber unit or it may be part of the impulse drive means of a jet injection device.

Figure 5:
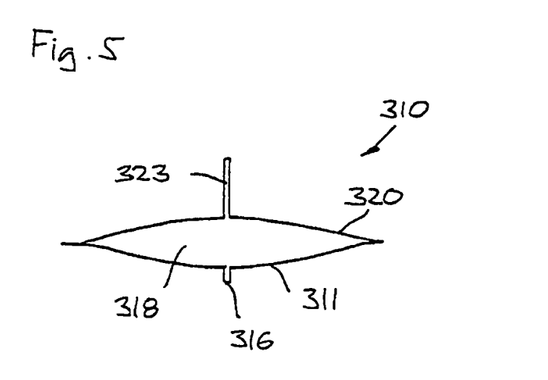

In FIG. 5 a further embodiment of an impulse chamber unit 310 is shown. The unit comprises two housing portions 311, 320 having a general configuration corresponding to Belleville springs sealed to each other at the peripheries thereof, an impulse chamber 318 being formed therebetween. The lower (distal) housing comprises an outlet nozzle 316 and the upper (proximal) housing comprises a fluid inlet in the form of a protruding back needle 323 extending from the diaphragm and into a septum of a cartridge (not shown). In this way a variable volume impulse chamber is provided in which both of the chamber-defining members move as the impulse chamber is filled and emptied. As described above, the protruding back needle allows the upper housing portion to move relative to a septum through which the back needle is arranged. When the impulse chamber has been filled with an amount of drug, it is expelled by forcing the two housing portions against each other (by means not shown) thereby creating e.g. a skin-penetrating jet or an aerosol of liquid drug.

Figure 6:
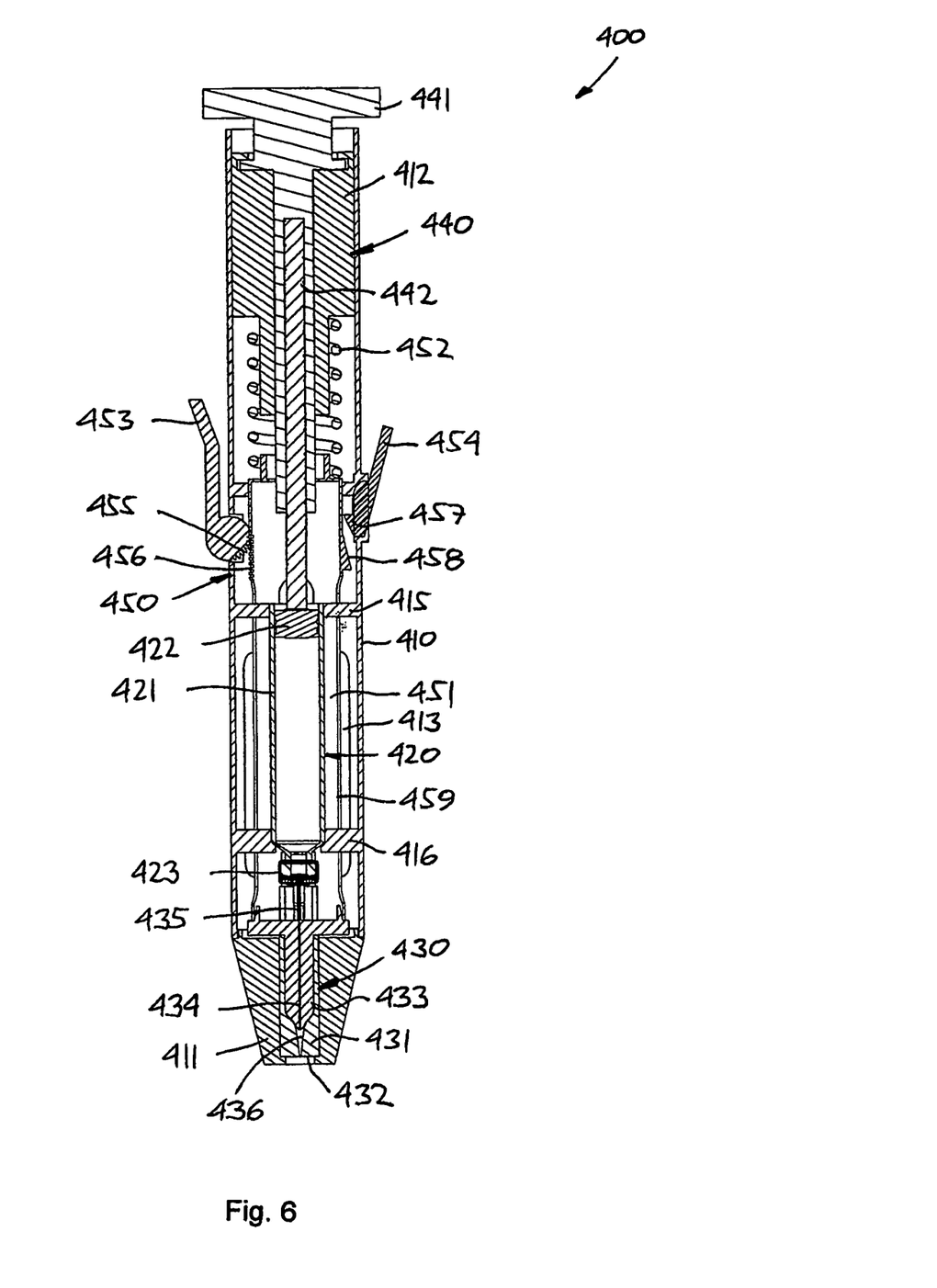
FIG. 6 shows a jet expelling assembly in a sectional view.

With reference to FIG. 6 a jet expelling assembly 400 will be described. The assembly comprises a housing 410 in which are arranged a reservoir 420 containing a fluid drug, an impulse chamber assembly 430 in fluid communication with the reservoir, a dose setting assembly 440 and an impulse generating assembly 450. The reservoir is in the form of a columnar cartridge 421 in which a piston 422 is slidably received, the reservoir comprising a distal outlet 423 in the form of a needle-penetratable septum. The reservoir is supported by housing supports 415, 416. The dose setting assembly comprises a user actuatable dial member 441 rotationally mounted in a proximal portion 412 of the housing, the dial member being in threaded engagement with a plunger 442, such that clockwise turning of the dial member will move the plunger and thereby the piston distally to expel an amount of fluid from the reservoir. The dose setting assembly preferably comprises a mechanism preventing the dial member to be turned anti-clockwise during normal use. If the cartridge is replaceable the dose setting assembly will have to be resettable.

The impulse chamber assembly comprises a chamber portion 431 with a distal fluid outlet nozzle 432, the chamber portion defining a cavity, and an impulse piston 433 slidably received in the cavity along a general axis, the piston comprising a through-going channel 434 in fluid communication with a generally straight conduit 435 protruding proximally from the piston and arranged generally in parallel with the general axis. The conduit is adapted to slidably engage the reservoir outlet during relative movement between the piston and the reservoir. The cavity and the piston in combination define a variable-volume impulse chamber 436. In the shown embodiment the nozzle is formed integrally with the chamber portion. When delivered to the user, the impulse chamber further comprises a removable closure member (not shown) sealing the nozzle outlet. The chamber portion is mounted in the housing by means of a mounting member 411 releasable connected to the distal end of the housing, the chamber portion thereby being arranged stationary relative to the reservoir. By this arrangement expelling an amount of drug from the reservoir to the impulse chamber via the conduit causes the piston to move proximally towards the reservoir, the impulse chamber thereby receiving the expelled amount of drug.

The impulse generating assembly 450 comprises a displaceable transfer tube 451, a spring 452, an actuation lever 453, and a release member 454. The transfer tube comprises longitudinal side openings 459 allowing it to move longitudinally relative to the housing supports for the reservoir. The spring engages the proximal end of the transfer tube and forces it distally towards the piston. The lever is pivotally connected to the housing and comprises a toothed portion 455 in engagement with a correspondingly toothed portion 456 on the transfer tube. The release member is pivotally connected to the housing and comprises a hook 457 adapted to engage a corresponding hook 458 on the transfer tube. As the housing comprises transparent portions 413 it is possible to inspect the contents of a transparent reservoir through the side openings in the transfer tube.

In a situation of use a new impulse chamber assembly is mounted in the housing. The user then actuates the impulse generating assembly by pivoting the actuation lever in the distal direction, this resulting in the transfer tube being moved proximally against the force of the spring to an energized position in which it is locked by engagement with the release member. Preferably a coupling (not shown) is provided in the actuation lever allowing the lever to be returned to its initial position after actuation as well as allowing the transfer tube to move distally without moving the lever. Thereafter the user transfers a desired dose of drug from the reservoir to the impulse chamber by rotating the dial member a desired number of increments, this moving the impulse piston proximally as described above. The maximum amount of drug which can be transferred to the impulse chamber is determined by the allowed travel of the impulse piston. In the filled position there should still be a distance between the impulse piston and the transfer tube as the transfer tube should be allowed to accelerate before acting upon the impulse piston to create the desired impulse. Thus a stop mechanism (not shown) may be provided limiting travel of the impulse piston. As appears from FIG. 6 a small amount of air is initially enclosed between the distal end of the piston and the nozzle, however, this amount of air is very small and is not harmful should such an amount of air be injected with the drug. As a final step in preparing the device for injection the user removes the nozzle seal. The nozzle is then placed against a desired skin surface where after the user releases the release member, this resulting in the transfer tube being moved distally by the spring, this expelling the drug contained in the impulse chamber through the nozzle and thereby through the skin and into the subcutis.

The jet expelling assembly may be a disposable prefilled device as shown, or it may be adapted for used with replaceable cartridges, e.g. by making the distal supports 415 of the housing operatable between an open and a closed position.

The jet expelling assembly of FIG. 6 comprises a single spring providing both an initial impulse to the impulse chamber and the force to empty the impulse chamber once the skin has been penetrated by a jet of drug. Alternatively a jet expelling assembly for injecting fluid medicament into a patient in a two-stage process may be provided. During the first stage fluid is expelled from the injector under relatively high pressure, to create an opening through the skin of the patient. During the second stage, fluid is infused through the opening into the patient at a lower pressure, and for a longer period of time. For example, U.S. Pat. No. 5,911,703, hereby incorporated by reference, discloses a jet expelling assembly with an impulse/drive mechanism including two springs which are positioned to urge against the impulse chamber piston as they elongate. The drive mechanism comprises a transfer rod (i.e. corresponding to the transfer tube of the above-described FIG. 6 embodiment) driven by two coaxially positioned separate springs, which are engaged with the rod. Specifically, the first of the two coaxial springs is an impulse spring which is characterized by a relatively high spring constant and the fact that it is dimensioned to have a relatively short action distance. In comparison with the first spring, the second spring, an injection spring, has a lower spring constant and a longer action distance. Initially, during acceleration of the transfer rod, both the impulse spring and the injection spring push on the rod. However, it is primarily the force of the impulse spring that accelerates the rod. The impulse spring expands until the impulse spring is restrained by a spring stop. After the impulse spring is stopped from expanding, the rod continues moving through a coast distance, until the rod collides with the impulse piston. As a result of this collision, the momentum of the transfer rod causes the piston to accelerate very rapidly. This rapid advancement of the piston is referred to as the impulse stage, and is the first of two stages of advancement of the piston. The impulse stage is very brief, e.g. less than about five milliseconds. Due to the rapid advancement of the piston during the impulse stage, the fluid is expelled through the jet nozzle under high pressure creating a hole or an opening in the skin. After the impulse stage, the injection spring continues to expand and push against the transfer rod. The result is a second stage, referred to as the injection stage. During the injection stage, the injection spring exerts a much smaller force against the rod and piston than the force which was exerted on the piston during the impulse stage. Accordingly, fluid medicament is expelled from the impulse chamber at a much lower pressure and at a much lower rate than during the impulse stage. The duration of the injection stage is much longer than the duration of the impulse stage, and can last as long as five seconds, or longer. During the injection stage, fluid medicament is allowed to slowly infiltrate into the subcutaneous tissue. As appears, such a two-spring two-stage mechanism may be used as an alternative to the one-spring mechanism disclosed in present FIG. 6.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A jet expelling assembly, comprising:
   a housing,
   a reservoir adapted to contain a fluid drug and comprising an outlet, and an impulse chamber assembly comprising:
      a chamber portion defining a cavity having a general axis,
      a piston slidably received in the cavity along the general axis and comprising a fluid inlet and a fluid outlet, the cavity and the piston in combination defining a variable-volume impulse chamber, the inlet comprising a generally straight conduit protruding from the piston and arranged generally in parallel with the general axis, the conduit being adapted to slidably engage the reservoir outlet during relative movement therebetween, and
      a fluid outlet nozzle in fluid communication with the impulse chamber,
   wherein the reservoir outlet comprises a self-sealing septum, and the conduit comprises a pointed proximal end adapted to penetrate the self-sealing septum, wherein the self-sealing septum is adapted to reseal itself, and
   wherein when expelling an amount of drug from the reservoir to the impulse chamber via the inlet the chamber portion is arranged stationary relative to the reservoir, and the piston moves towards the reservoir, the impulse chamber thereby receiving the expelled amount of drug.

2. A jet expelling assembly as in claim 1, wherein the conduit is arranged generally co-axially with the general axis.

3. A jet expelling assembly as in claim 1, wherein the fluid outlet nozzle is arranged generally in parallel with the general axis.

4. A jet expelling assembly as in claim 1, wherein the conduit is formed integrally with the piston.

5. A jet expelling assembly as in claim 1, wherein the fluid inlet comprises a uni-directional inlet valve, a constriction or a tortuous path portion.

6. A jet expelling assembly as in claim 1, wherein the fluid outlet nozzle comprises a pointed hollow needle adapted to penetrate a superficial layer of the skin of a user.

7. A jet expelling assembly as in claim 1, further comprising an expelling assembly for expelling an amount of drug from the reservoir to the impulse chamber via the fluid inlet thereby expanding the impulse chamber, and an impulse generating assembly adapted to actuate the piston to thereby reduce the volume of the impulse chamber, thereby expelling an amount of drug through the outlet nozzle.

8. A jet expelling assembly as in claim 7, wherein the fluid outlet nozzle is adapted to be arranged against the skin of a subject, the impulse generating assembly being adapted to create a force for injecting the liquid drug from said impulse chamber, through the outlet nozzle and into the subject through the skin.

9. A jet expelling assembly as in claim 8, further comprising a drive assembly for reducing the volume of the impulse chamber with a reduced force relative to the impulse generating assembly when a portion of the drug has been expelled by the impulse generating assembly.

10. A jet expelling assembly as in claim 9, further comprising a dose setter for selectably setting a dose of drug to be expelled and transfer that amount of drug to the impulse chamber, an actuator for actuating the impulse generating assembly and the drive assembly, and an actuatable release, wherein actuation of the release causes the impulse generating assembly to expel a portion of the set dose from the impulse chamber at a high pressure through the outlet nozzle, followed by subsequent expelling of the remaining portion of the set dose from the impulse chamber through the outlet nozzle by means of the drive assembly.

11. A jet expelling assembly as in claim 7, wherein the impulse generating assembly comprises a coil spring arranged substantially axially relative to the general axis.

12. A jet expelling assembly as in claim 7, wherein the fluid inlet is an open communication allowing an amount of drug to be forced backwardly into the reservoir during expelling of drug from the impulse chamber, the flow resistance of the outlet nozzle, the flow resistance of the fluid inlet and the impulse generating assembly being configured to allow a backflow selected from the group of ranges consisting of less than 15%, less than 10%, less than 5% and less than 1%.

13. A jet expelling assembly as in claim 1, wherein the impulse chamber assembly is releasably attached relative to the housing.

14. A jet expelling assembly as claim 1, wherein the reservoir is releasably attached relative to the housing.

15. A jet expelling assembly as in claim 1, wherein the reservoir has a general columnar configuration with a longitudinal axis arranged generally in parallel with the axis defined by the movement of the piston.

16. A method for expelling an amount of drug, comprising:
   providing a jet expelling assembly comprising:
      a drug reservoir with an outlet, the reservoir outlet comprising a self-sealing septum,
      a variable-volume impulse chamber arranged stationary relative to the reservoir when expelling an amount of drug from the reservoir to the impulse chamber via an inlet, the variable-volume impulse chamber further comprising an axially displaceable piston, the piston in sliding engagement with the reservoir outlet and having a conduit with a pointed proximal end adapted to penetrate the self-sealing septum of the reservoir for fluid communication between the reservoir and the variable-volume impulse chamber, wherein the self-sealing septum is adapted to reseal itself, and
      a nozzle in fluid communication with the impulse chamber,
   whereby expelling an amount of drug comprises moving the piston towards the reservoir to expel an amount of drug from the reservoir to the impulse chamber, and moving the piston away from the reservoir to expel an amount of drug from the impulse chamber through the nozzle.

17. A jet expelling assembly, comprising:
   a housing including at least one longitudinal slot,
   a reservoir adapted to contain a fluid drug and comprising an outlet, and an impulse chamber assembly comprising:

a chamber portion defining a cavity having a general axis, a piston slidably received in the cavity along the general axis and comprising a fluid inlet and a fluid outlet, the cavity and the piston in combination defining a variable-volume impulse chamber, the inlet comprising a generally straight conduit protruding from the piston and arranged generally in parallel with the general axis, the conduit being adapted to slidably engage the reservoir outlet during relative movement therebetween, and the piston including at least one radial projection adapted to slidably engage the at least one longitudinal slot of the housing, and a fluid outlet nozzle in fluid communication with the impulse chamber, wherein the reservoir outlet comprises a self-sealing septum, and the conduit comprises a pointed proximal end adapted to penetrate the self-sealing septum, wherein the self-sealing septum is adapted to reseal itself, and wherein when expelling an amount of drug from the reservoir to the impulse chamber via the inlet, the chamber portion is arranged stationary relative to the reservoir, and the piston moves towards the reservoir along the at least one longitudinal slot of the housing, the impulse chamber thereby receiving the expelled amount of drug.

18. A method for expelling an amount of drug, comprising:

slidably receiving a piston in a cavity along a general axis, wherein:

the piston comprises a fluid inlet and a fluid outlet;

a housing includes at least one longitudinal slot; and a reservoir is adapted to contain a fluid drug and comprises an outlet and an impulse chamber assembly, wherein:

a chamber portion defines the cavity along the general axis;

the cavity and the piston in combination define a variable-volume impulse chamber;

the inlet comprises a generally straight conduit protruding from the piston and arranged generally in parallel with the general axis;

the conduit is adapted to slidably engage the reservoir outlet during relative movement therebetween;

the piston comprises at least one radial projection adapted to slidably engage at least one longitudinal slot of the housing;

the reservoir outlet comprises a self-sealing septum; and the conduit comprises a pointed proximal end adapted to penetrate the self-sealing septum, wherein the self-sealing septum is adapted to reseal itself, wherein when expelling an amount of drug from the reservoir to the impulse chamber via the inlet, the chamber portion is arranged stationary relative to the reservoir, and the piston moves towards the reservoir along the at least one longitudinal slot of the housing, the impulse chamber thereby receiving the expelled amount of drug.

* * * * *